United States Patent
Schenker et al.

(10) Patent No.: US 10,596,327 B2
(45) Date of Patent: Mar. 24, 2020

(54) INJECTION DEVICE WITH A DOSING MEMBER AND A PRETENSIONED DISCHARGE SPRING

(71) Applicant: TecPharma Licensing AG, Burgdorf (CH)

(72) Inventors: Susanne Schenker, Langenthal (CH); Ursina Streit, Schonbuhl (CH)

(73) Assignee: TecPharma Licensing AG, Burgdorf (CH)

( * ) Notice: Subject to any disclaimer, the term of this patent is extended or adjusted under 35 U.S.C. 154(b) by 73 days.

(21) Appl. No.: 15/173,333

(22) Filed: Jun. 3, 2016

(65) Prior Publication Data

US 2016/0279339 A1    Sep. 29, 2016

Related U.S. Application Data

(63) Continuation of application No. PCT/CH2014/000165, filed on Nov. 14, 2014.

(30) Foreign Application Priority Data

Dec. 5, 2013    (EP) .................................... 13195951

(51) Int. Cl.
*A61M 5/315*  (2006.01)
*A61M 5/20*   (2006.01)
*A61M 5/31*   (2006.01)

(52) U.S. Cl.
CPC .......... *A61M 5/31553* (2013.01); *A61M 5/20* (2013.01); *A61M 5/3158* (2013.01); *A61M 2005/3126* (2013.01)

(58) Field of Classification Search
CPC .... A61M 5/20; A61M 5/2033; A61M 5/3155; A61M 5/31553; A61M 5/31556;
(Continued)

(56) References Cited

U.S. PATENT DOCUMENTS 6,280,421 B1 *  8/2001 Kirchhofer ......... A61M 5/2033
                                              604/187
9,623,185 B2 *  4/2017 Raab ....................... A61M 5/24
(Continued)

FOREIGN PATENT DOCUMENTS

EP    1681070 A1    7/2006
EP    2644217 A1   10/2013
(Continued)

OTHER PUBLICATIONS

International Search Report dated Dec. 12, 2014 for International Application No. PCT/CH2014/000165, 3 pages.
(Continued)

*Primary Examiner* — Kevin C Sirmons
*Assistant Examiner* — Tezita Z Watts
(74) *Attorney, Agent, or Firm* — Dorsey & Whitney LLP

(57) ABSTRACT

A drive and dosing device is described for an injection device for administering a fluid product, in particular a medication, wherein the drive and dosing device can be adjusted to a product dose to be administered. The drive and dosing device has, among other things, a coupling which, upon activation of an activation element, enables rotation of a rotation element relative to a housing, wherein by disengaging the activation element, the rotation of the rotation element relative to the housing is blocked.

18 Claims, 5 Drawing Sheets

(58) Field of Classification Search
CPC .......... A61M 5/31585; A61M 5/31583; A61M 5/31573; A61M 2005/202; A61M 2005/3125; A61M 2005/3126
See application file for complete search history.

(56) References Cited

U.S. PATENT DOCUMENTS

| | | | |
|---|---|---|---|
| 2009/0149809 A1* | 6/2009 | Bollenbach | A61M 5/2033 604/111 |
| 2010/0137798 A1* | 6/2010 | Streit | A61M 5/2033 604/110 |
| 2016/0051766 A1* | 2/2016 | Marsh | A61M 5/31583 604/207 |

FOREIGN PATENT DOCUMENTS

| | | |
|---|---|---|
| WO | 01/19434 A1 | 3/2001 |
| WO | 2009141005 A1 | 11/2009 |
| WO | 2010149209 A1 | 12/2010 |
| WO | 2013144020 A1 | 10/2013 |
| WO | 2013144021 A1 | 10/2013 |

OTHER PUBLICATIONS

International Preliminary Report dated Jun. 7, 2016 for Patentability for International Application No. PCT/CH2014/000165, 3 pages.

* cited by examiner

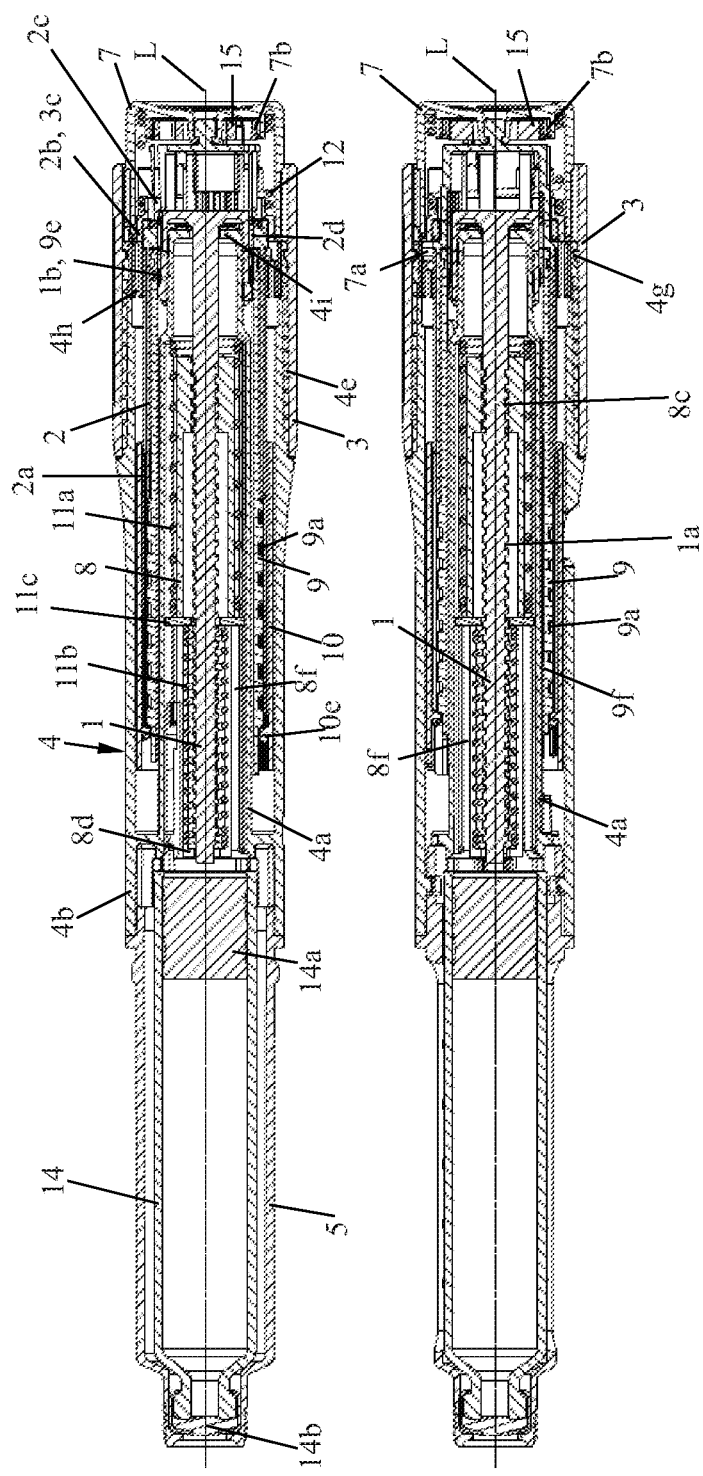

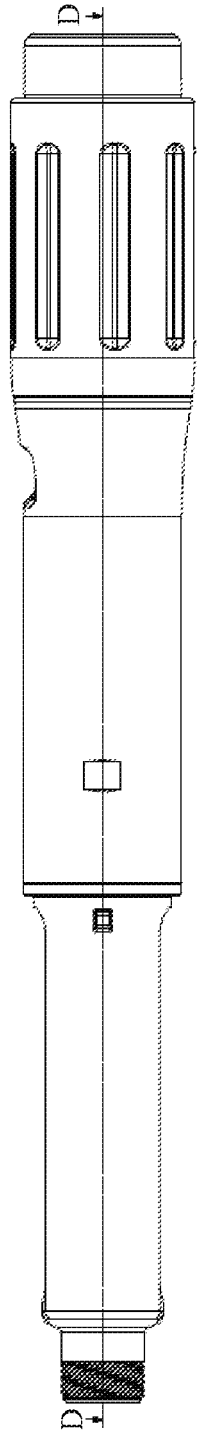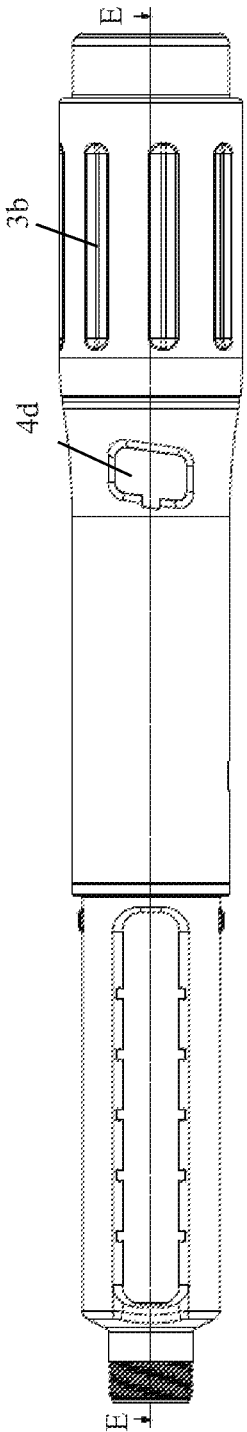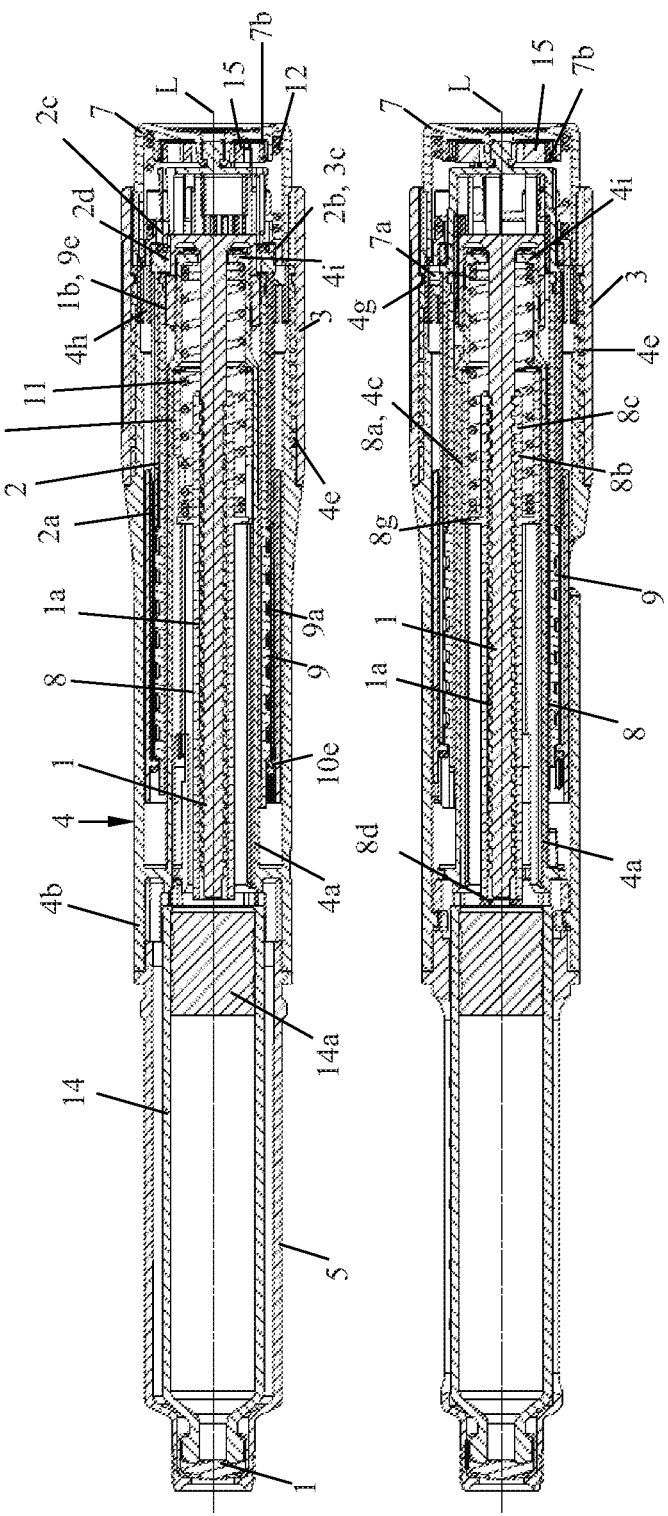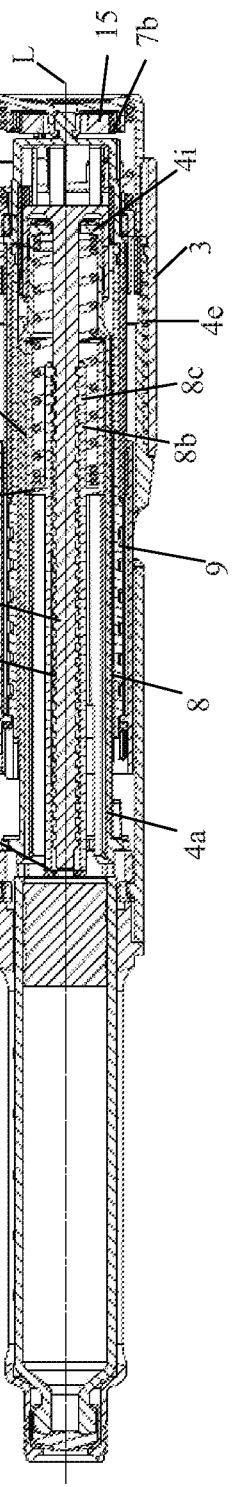
Figure 3A
Figure 3B
Figure 3C
Figure 3D

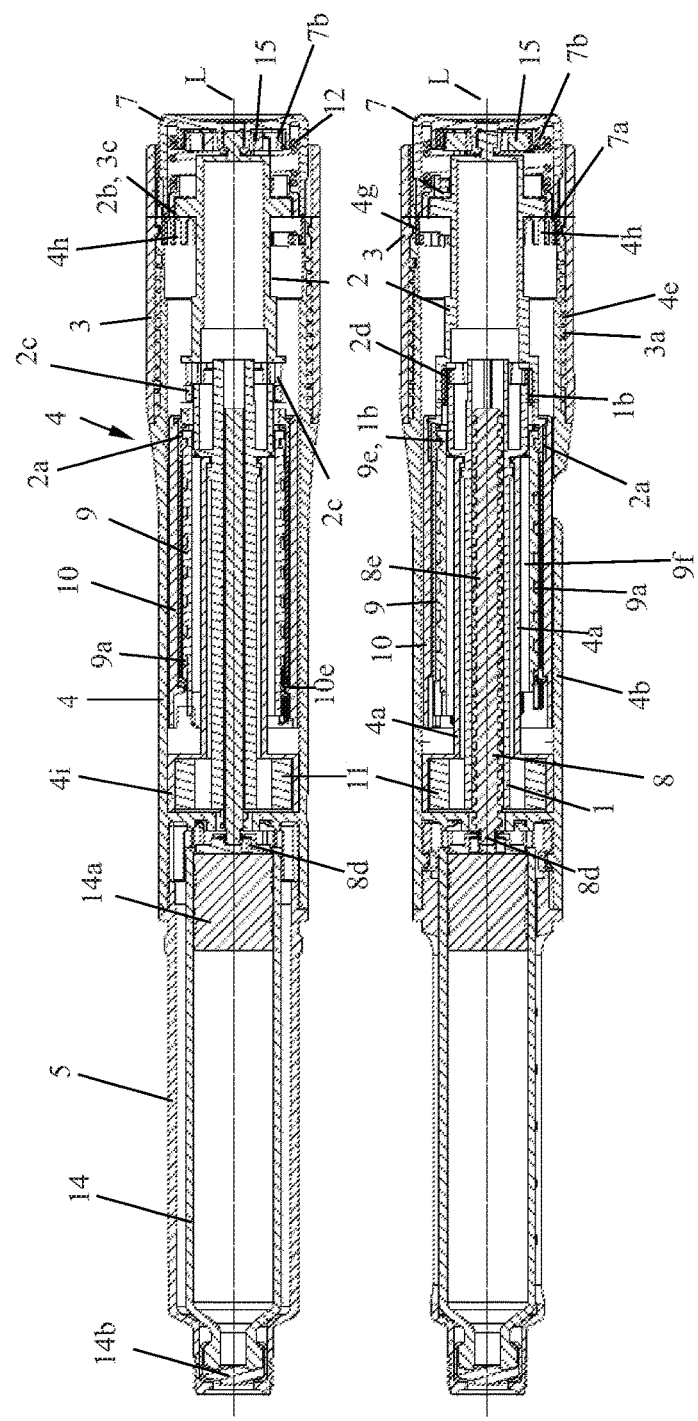

INJECTION DEVICE WITH A DOSING MEMBER AND A PRETENSIONED DISCHARGE SPRING

CROSS-REFERENCE TO RELATED APPLICATIONS

This application is a Continuation of International Patent Application No. PCT/CH2014/000165 filed Nov. 14, 2014, which claims priority to European Patent Application No. 13195951.2 filed Dec. 5, 2013, the entire contents of each are incorporated herein by reference for any and all purposes.

BACKGROUND

The invention concerns an injection device for administration of a liquid product, in particular a medication such as insulin for diabetes treatment. In particular, the invention concerns a drive and dosing device for such an injection device.

The term "medication" here comprises any flowable medicinal formulation that is suitable for controlled administration through a means like a cannula or hollow needle, for example a liquid, a solution, a gel, or a fine suspension that contains one or more medicinal agents. "Medication" can be a composition having a single active agent or a premixed or co-formulated composition having a plurality of active agents from a single container. "Medication" comprises drugs like peptides (for example, insulins, insulin-containing medications, GLP-1-containing as well as derivative or analogous preparations), proteins and hormones, biologically obtained or active agents, agents based on hormones or genes, nutrient formulations, enzymes, and other substances both in solid (suspended) or liquid form, and also polysaccharides, vaccines, DNA or RNA, or oligonucleotides, antibodies or parts of antibodies, as well as suitable basic agents, adjuvants, and vehicles.

The invention is a further development of the invention described in the patent application having publication number WO 2013/144021 A1.

SUMMARY

In prior approaches, it was problematic to provide a drive and dosing device for an injection device for administration of a liquid product that allows for the simple use of the device for the user, in particular simple dose selection, while still providing a compact construction.

This problem is solved by the features of the claims, as well as the further developments provided in the description and the figures.

The invention originates from a drive mechanism for an injection device for administration of a liquid medication or product. The drive mechanism has a housing. The housing is preferably sleeve-shaped and/or elongated. The housing can, for example, extend along its lengthwise axis.

The housing can optionally accommodate a product container or itself form the product container. The housing can be made in one piece or have a plurality of parts. For example, the housing can form a proximal housing part that comprises or has the drive and dosing device. The housing can additionally have a product container holder, which accommodates the product container, for example a cartridge, and is connected to the housing or the proximal housing part. The said connection can be such that the product container holder and the housing or the proximal housing part cannot be separated after being connected, i.e., they can be separated only by destroying the connecting elements. Such a solution is advantageous in particular in the case of one-way, disposable injection devices, which are discarded in their entirety after the product contained in the product container has been completely discharged. Alternatively, the product container holder can also be separably affixed to the housing, so that it is possible, although less preferable, to use the drive and dosing device a number of times, i.e., to exchange an empty product container for a full product container.

The housing is preferably intended to be held by the user of the device. In particular, the housing can have an essentially cylindrical shape. The housing can have, for example, an indicator device, in particular a window, by means of which or through which a currently selected dose can be read, preferably on a scale of a dose selection element.

In a first aspect, which, for example, advantageously develops the invention further, the drive and dosing device, which in particular together with the product container forms an injection device, comprises, besides a housing, a dose display element over the circumference of which a dose scale is disposed. The dose display element may be ring-shaped in cross section. The dose display element may be a dose display drum or a dose display ring. The dose scale can extend over the circumference of the dose display element, preferably helically. The dose scale preferably comprises a plurality of values that are arranged in succession. Preferably, these are numerical values that specify the desired product dose in international units (IU) or in milligrams.

Alternatively, the dose scale can be disposed without a pitch over the extent of the dose display element, for example the dose display ring, in which case the scale values then repeat after one rotation of the dose display element. In the case of a dose scale with a pitch, i.e., a helical dose scale, the dose display element, in particular the dose display drum can be turned more than one rotation without the scale values repeating, so that the scale values can advantageously represent larger or more scale values.

The drive and dosing device further comprises an indicator device, where the dose display element for selecting the dose to be administered can be rotated relative to the indicator element, in particular about an axis of rotation that preferably corresponds to the lengthwise axis of the drive and dosing device and/or the dose display element. In this case this can be a pure rotary motion, i.e., a rotary motion without a superimposed axial motion. Preferably, the rotary motion is superimposed by an axial motion, so that the dose display element can be screwed relative to the indicator device to select the dose to be administered. A screwable dose display element can advantageously be combined with a helical dose scale, where the screw motion and the dose scale advantageously have the same pitch. A dose display element that can be turned without axial motion can advantageously be combined with a zero-pitch dose scale.

By means of the indicator device, which is preferably formed on the housing, one can read a value of the dose scale that corresponds to the selected dose. The indicator device can, for example, be a window, which can be formed by an opening in the housing or by a transparent insert. Alternatively or optionally, the indicator device can be an arrow or have an arrow, which marks the value of the dose scale that corresponds to the selected dose, for example, in addition to the window. This is advantageous in order to guarantee an unambiguous dose selection, for example, if another value still appears at least partially in the window. The indicator can be, for example, a projection or an imprint or a notch or the like.

The drive and dosing device comprises a dosing member, which is made as a dosing button and can optionally be called the dose selection member. The dosing member can preferably be held by the user (patient, physician, medical personnel) of the drive and dosing device and preferably forms an external, especially externally accessible, surface of the drive and dosing device. To select the dose to be discharged or administered, the dosing member is preferably held by the user and turned relative to the housing, and in particular the indicator device, about an axis of rotation, which may correspond to the lengthwise axis of the elongated drive and dosing device. The dosing member is preferably connected to the housing in an axially fixed way, in particular is not able to move along a lengthwise axis of the housing, so that intuitive handling of the device by the user is advantageously facilitated, since one merely needs to make a rotary motion of the dosing member to select a dose.

In particular, the dose display element can be non-rotatably connected or coupled to the dosing member, but, for example, in an axially movable way, at least during dose selection. For intuitive use it is advantageous if, when the dosing member is rotated by an angle of rotation, the dose display element is likewise rotated by the same angle of rotation.

The drive and dosing device can have an actuation member, for example in the form of an actuation button. The actuation member can form an external surface of the drive and dosing device and/or be accessible externally. The actuation member can be formed at the proximal end, in particular the rear end of the drive and dosing device or form the said end. The actuation member in this way can advantageously be actuated, in particular pressed, with the thumb of the hand that holds the housing. The actuation is stopped by releasing the actuation member. "Actuation" is understood to mean the moving of the actuation member in the drive and dosing device, in particular in the distal direction, so that in particular a product discharge can be produced. The actuation member is advantageously movable relative to the dosing member and in particular can be accommodated by the dosing member so that it can move axially.

The actuation member can advantageously move, in particular be actuated, against the force of a spring, in particular a reset or coupling spring, so that the said spring becomes tensioned. Upon releasing the actuation member, the said spring can reset it, in particular relative to the dosing member, in particular in the proximal direction or away from the drive and dosing device.

The drive and dosing device additionally comprises a bearing element, with which the dose display element engages. The engagement advantageously brings about the rotary or sliding motion of the dose display element relative to the indicator device. For example, the engagement between the dose display element and the bearing element can be a threaded engagement. In particular, the bearing element can have an external thread and the dose display element an internal thread, where the threads mesh with each other and in this way cause the dose display element to be screwable relative to the bearing element.

In particular, the dose display element can rotate or screw back and forth between a maximum dose position and a zero dose position. In the zero dose position, advantageously, the dose or the figure "0" can be read in the indicator device. In the maximum dose position, the maximum product dose that can be discharged using the drive and dosing device can advantageously be read.

In the zero dose position, the dose display element is blocked against rotation in a direction of rotation, namely in the direction of rotation that would cause a dose smaller than zero to be selected. In the zero dose position, the dose display element can preferably be moved only in the direction of rotation that brings about an increase of the dose. In the maximum dose position, the dose display element is preferably blocked against rotation in a direction of rotation, namely in the direction of rotation that would cause the selection of a dose greater than the maximally selectable dose. In the maximum dose position, the dose indicator element can be rotated in particular only in the direction of rotation that brings about a reduction of the product dose.

The dose display element can have, for example, a stop which abuts a counterstop in the zero dose position and thus prevents the rotation in a direction of rotation. The same or an additional stop can prevent the rotation of the dose display element beyond the maximum dose. In particular, another counterstop, namely a maximum dose counterstop, can be provided. Correspondingly, the other counterstop can be called the zero dose counterstop. Accordingly, the dose display element can have a zero dose stop for the zero dose counterstop and a maximum dose stop for the maximum dose counterstop. Preferably, the stop or stops act in the circumferential direction and/or in the axial direction.

The drive and dosing device according to the first aspect can preferably be configured so that the bearing element can move together with the dose display element relative to the housing and along the axis of rotation, in particular in the distal direction. This aspect can advantageously develop the drive and dosing device further according to a second aspect described herein. Alternatively, the dose display element can have a thread, which is engaged with the housing. Through this, the dose display element can screw back and forth relative to the housing, but cannot move, in particular in a purely axial motion, independently from the screwing motion.

Preferably, the actuation member is coupled to the bearing element so that a movement of the actuation member relative to the housing and/or the dosing member causes a movement of the bearing element relative to the housing and/or the dosing member, in particular along the lengthwise axis of the drive and dosing device.

Because the dose display element is engaged with the bearing element, in accordance with the invention, and the bearing element can move relative to the housing and along the axis of rotation, the dose display element can also move relative to the housing and along the axis of rotation independently from the rotating or screwing motion that the dose display element makes during the selection of a dose. The drive and dosing device according to the second aspect, however, can basically also be advantageously combined with the alternative dose display element, which is in a threaded engagement with the housing or an element affixed to the housing. In this alternative, the bearing element can be formed by the housing or be a part of the housing, where the bearing element can be non-rotatable and axially fixed with respect to the rest of the housing.

Advantageously, a moving of the bearing element together with the dose display element can be read at the indicator device and/or the dose display element. Through this, the user can monitor the operating state of the drive and dosing device, i.e., whether the drive and dosing device, in particular the actuation member, is actuated or unactuated.

In a preferred variation, the actuation member and/or the bearing element can move together with the dose display element relative to the indicator device and the housing and along the axis of rotation. In the region of the indicator device, in particular in the window of the indicator device, a marking that is different from the dose scale can appear when the bearing element has moved. The marking is preferably disposed on the dose display element. If the bearing element has not moved, in particular the drive and dosing device is unactuated for a product discharge, the marking can be disposed outside the indicator device, i.e., for example, covered by a housing or another element. If the bearing element is moved, in particular the drive and dosing device for product discharge is actuated, the marking can emerge from the covered region, so that it can be seen or be readable in particular in or on the indicator device. If the actuation of the drive and dosing device is interrupted or stopped, the bearing element can return to the original position, so that the marking is preferably removed from the region of the indicator device and in particular becomes covered.

In an alternative variation, the actuation member and/or the bearing element can move together with the dose display element and the indicator device relative to the housing and along the axis of rotation. The indicator device can, for example, be a lens or at least function as a lens. For example, the indicator device can be connected with the bearing element at least so that it cannot move axially, preferably also so that it cannot rotate. Basically, the bearing element can form the indicator device. Of course, it is also possible for the indicator device to be a part that is separate from the bearing element. The indicator device can, for example, be sleeve-shaped.

In this variation, the moving of the bearing element can bring about the appearance, in the region of the indicator device, of a marking that is different from the dose scale, which is disposed at or on the indicator device. For example, the indicator device can be disposed inside the housing. The marking of the indicator device can be covered by the housing or another element in the unactuated state of the drive and dosing device. If the drive and dosing device, in particular the actuation member, becomes actuated, so that the dose display element is moved together with the indicator device, the marking can emerge from its covering, so that the marking becomes visible or readable. If the actuation is interrupted or stopped, the dose display element, together with the indicator device and the bearing element, can be moved back into their starting position, so that the marking again is disposed under the covering.

Generally preferably, a spring, in particular a coupling or reset spring, can be tensioned during the actuation of the drive and dosing device for a product discharge. In other words, the bearing element can be moved against the force of such a spring during the actuation, in particular from an unactuated position to an actuated position. The spring can be, for example, a coil or helical spring, which acts as a compression spring. The spring further acts to return the bearing element to its starting position or an unactuated position if the actuation is interrupted or stopped. In particular, the bearing element is moved in the distal direction upon actuation. The bearing element is moved back in the proximal direction if the actuation is interrupted or stopped.

The actuation of the actuation member causes the bearing element, together with the dose display element, to be moved relative to the housing and along the axis of rotation. In the broader sense, the actuation of the actuation member can cause a driven member, whose distal end is intended to act on a piston in the product container, which is affixed or can be affixed to the drive and dosing device, to be moved in the distal direction, in particular the discharge direction. The actuation member can, for example, be disposed at the proximal, i.e., rear end of the drive and dosing device or can form the proximal end of the drive and dosing device. Alternatively, the actuation member can be disposed on the side of the housing and/or between the distal end and the proximal end of the drive and dosing device. In general, the actuation member can be formed as a kind of actuation button. The actuation member is preferably moved during the actuation relative to the housing or the dosing member. In particular, the user of the device can actuate the actuation member advantageously, for example with the thumb of the hand that is holding the housing of the drive and dosing device.

The actuation member is preferably connected to the bearing element so that it moves the bearing element during actuation, in particular via a coupling member, which can, for example, be connected rotatably and axially fixed to the bearing element.

In generally preferred embodiments, the activation of the actuation member can cause the dose display element to rotate relative to or at the bearing element or the housing, in particular to be screwed, in particular in a direction that counts down the dose scale values that pass by at the indicator device during the rotary motion. Preferably, the angle of rotation of the dose display element and the discharge stroke of the driven member are in a proportional relationship, in particular at every point in time during the dose discharge. This results in a real-time display that counts back during the dose discharge until it finally reaches a value of 0, where the discharge of the dose is then stopped. If the actuation for the discharge is interrupted during the reverse rotation of the dose display element, the dose display element shows the amount still remaining for the discharge of the said dose.

In one variation, the drive and dosing device can be designed so that the energy needed to rotate the dose display element and/or to move the driven member in the distal direction is supplied manually, in particular by the user's force acting on the actuation member. For example, the dose selection element, in particular the dosing button, can be screwed out from the proximal end of the housing for a dose selection, where it becomes screwed back into the housing for dose discharge when the actuation member is actuated.

In a preferred alternative variation, the drive and dosing device can be configured so that the energy needed to rotate the dose display element back and/or to move the driven member in the distal direction is provided automatically, in particular by a spring, in particular a discharge spring, contained in the drive and dosing device. For example, the spring energy stored in the discharge spring can be transmitted to the dose display element and/or the driven member, so that the dose display element is rotated back and the driven member is moved in the distal direction. The discharge spring can be coupled, for example, with the dosing member so that a rotation of the dosing member during dose selection pretensions the discharge spring. The spring can then store the energy needed for the selected dose.

In a preferred alternative, the spring can already be pretensioned with enough energy for a plurality of discharges of the product dose, in particular for the discharge of the entire product that can be discharged from the product container when the drive and dosing device is delivered. In this alternative the dosing member can be uncoupled from the spring during dose selection, i.e., not be coupled with the discharge spring so that a rotation of the dosing member causes a tensioning of the spring. Through this, clearly less force on the part of the user is needed to rotate the dosing member in the selection of the dose.

The dosing member, in particular the dosing button, can surround or hold the actuation member, in particular the actuation button. In this way the dosing member and the actuation member can form the proximal end of the drive and dosing device. Preferably, the actuation member can be moved relative to the dosing member for actuation.

In embodiments in which the energy needed for discharge is automatically provided, the dosing member can preferably be disposed in an axially fixed but rotatable way relative to, in particular on, the housing.

In a second aspect, from which in particular this invention originates and which can be combined with the features of the first aspect, in particular with or without the feature that the bearing element can be moved together with the dose display element relative to the housing and along the axis of rotation, the drive and dosing device can have a driven member, whose distal end is intended to act on a piston, in particular directly or preferably indirectly. The piston can be a part of the product container that is affixed or can be affixed to the drive and dosing device, for example a cartridge. The driven member can in the broader sense be called a piston rod, and the driven member does not necessarily have to be massive, but rather can also be made hollow, for example sleeve-shaped. Optionally a, for example, rotatable flange, which presses against the piston, can be made at the distal end of the driven member. In general, it is preferred that the distal end of the driven member press against the piston. The driven member can preferably be movable relative to the housing along the lengthwise axis of the drive and dosing device.

The drive and dosing device can have an abutment and preferably a guide, where the driven member can be moved relative to the abutment and preferably also relative to the guide in a direction, in particular in the distal direction or in the discharge direction, in order to bring about a discharge of the selected product dose. Preferably, the driven member can be guided straight or axially along the lengthwise axis of the drive and dosing device by means of or on the guide. In particular, the driven member can be non-rotatable relative to the abutment and/or the guide and/or the housing. In an alternative embodiment, the driven member can be rotatable relative to the abutment or the housing in combination with a lengthwise motion, i.e., screwable relative to the abutment, although this is less preferred. In general, the guide and/or the abutment can be formed from the housing, in particular a sleeve-shaped housing part or, for example, a sleeve-shaped element affixed to the housing.

The driven member and the guide that is formed, in particular, by the housing can, for example, be in a direct or, via an intermediate element, in an indirect engagement, which prevents a rotation of the driven member relative to the abutment or the housing, but allows an axial motion or screw motion of the driven member relative to the abutment or the housing. The guide can, for example, be an axial guide or a thread with a non-self-locking thread pitch.

The guide or the housing segment that forms the abutment or/and the guide, in particular an inner sleeve, can preferably surround the driven member, for example surround it in a sleeve shape and/or be firmly affixed to the housing or be formed by the housing. Between the sleeve-shaped housing part and an external, preferably likewise sleeve-shaped housing part, there can be an annular gap, which holds the advantage that an optional dose display element, in particular a dose display drum, can be accommodated therein. Because of this, the length of the drive and dosing device can be kept small.

According to the second aspect, the drive and dosing device can have at least one, for example exactly one, two, or three discharge springs acting and in particular disposed between the driven member or a rotation member and the abutment. The at least one spring can rest against the driven member and/or the abutment. For example, the discharge spring, if there is only one for example, can rest at its distal end against the driven member and at its proximal end against the abutment. In particular, the at least one discharge spring can be disposed inside the guide or the sleeve-shaped housing part that forms the guide. If the driven member is sleeve-shaped, the at least one discharge spring can be disposed inside the driven member. Alternatively, a first discharge spring and a second discharge spring can be operably disposed between the driven member and the guide or the sleeve-shaped housing part that forms the guide. The first discharge spring can, for example, surround the second discharge spring or vice versa. In particular, the second discharge spring can be disposed concentrically relative to the first discharge spring. The first discharge spring and the second discharge spring can, for example, be connected in parallel or in series. "Parallel connected discharge springs" means in particular that the first and the second discharge springs can respectively abut the driven member at their distal end and the abutment at their proximal end. In this way the spring constants of the first and second discharge springs can add up to a total spring constant. "Series connected discharge springs" means in particular that the distal end of one of the first and second discharge springs presses against the proximal end of the other of the first and second discharge springs, in particular directly or preferably indirectly, for example, via the intermediate element. For example, the first discharge spring rests against the abutment and the intermediate element and the second discharge spring rests against the intermediate element and the driven member. For example, the distal end of the first discharge spring can be disposed distal to the proximal end of the second discharge spring. Because of the intermediate element, the spring force of the first spring can be transmitted from its distal end to the proximal end of the second discharge spring. In particular, the intermediate element can be sleeve-shaped and can be disposed in an annular gap between the first and second discharge springs. Series connected discharge springs enable a spring force that remains relatively uniform over a relatively long spring path.

For example, the at least one discharge spring, in particular the first and second discharge spring, can be a helical or coil spring, which acts as a compression spring or as a torsion spring. The at least one discharge spring is pretensioned and thus acts on the driven member so that it attempts to move the driven member in the distal direction relative to the abutment, i.e., in the discharge direction. The at least one discharge spring, in the delivered state of the drive and dosing device, is pretensioned in particular with enough energy so that it can discharge the maximum or the entire dischargeable amount of product from the product container in several individual discharges, i.e., in particular in a plurality of discharges of individual product doses. The drive and dosing device is designed so that after each single discharge or discharge of the product dose, the next dose to be discharged is newly selected. In contrast to designs in which a discharge spring is newly pretensioned with each dose selection, a simpler dose selection can be achieved through the spring that is pretensioned with the energy necessary for discharge of the maximum amount of product that can be discharged from the product container, since the dosing member that is rotatable relative to the housing for dose selection is then easier to rotate because the spring does not have to be pretensioned during the dose selection. This improves ease of use for the user of the device.

The drive and dosing device can further comprise a rotation member, the rotation of which causes the drive spring to transmit energy to the driven member, due to which the driven member is moved in the distal direction. The rotation member preferably functions as a control element, where the rotation of the rotation member by a certain angle of rotation brings about the advance of the driven member by a certain discharge stroke. Through selective release or blocking of a rotation of the rotation member relative to the housing, the drive spring can be enabled so that it can move or not move the driven member in the distal direction relative to the abutment. In particular, the rotation member can be coupled to the actuation member so that during the actuation of the actuation member for a product discharge, it is released for a rotation relative to the housing and if the actuation member is not being actuated, it is blocked for a rotation relative to the housing. In particular, at least one coupling that causes the release and blocking of the rotation of the rotation member relative to the housing can be disposed between the actuation member and the rotation member.

Advantageously, the at least one coupling can release the rotation of the rotation member relative to the housing by actuation of the actuation member and block the rotation of the rotation member relative to the housing by releasing the actuation member.

According to a first sub-aspect, the at least one spring comprises a first helical compression spring and a second helical compression spring, where the first compression spring rests against the abutment and a second intermediate element and the second compression spring rests against the intermediate element and the driven member. The intermediate element can couple the driven member non-rotatably to the housing. The first compression spring can rest, for example, against the intermediate element at its distal end and, for example, against the intermediate element at its proximal end. In particular, the first compression spring and the second compression spring are connected in series. A compression spring is understood to mean a helical spring acting as a compression spring. The intermediate element can, for example, be ring-shaped and surround the driven member. In particular, the intermediate element can be disposed in an annular gap between an inner sleeve of the housing, which forms the guide, and the driven member.

In particular, the intermediate element can be engaged with the housing, in particular the inner sleeve and/or the guide, so that the intermediate element can move along the lengthwise axis relative to the housing and cannot rotate about the lengthwise axis. The intermediate element can be engaged with the driven member so that the intermediate element can move along the lengthwise axis relative to the driven member and cannot rotate about the lengthwise axis. Through this, the driven member is non-rotatably connected or coupled to the housing via the intermediate element.

The intermediate element is preferably in a floating position between the first spring and the second spring, so that the forces on the intermediate element exerted by the first spring and the second spring are cancelled out.

For example, the first compression spring can surround the driven member and the second compression spring can surround the driven member. This means that the first compression spring and the second compression spring can be disposed in the annular gap between the inner sleeve of the housing and the driven member. For example, the outside diameter of the first compression spring can be greater than the outside diameter of the second compression spring. Through this, the design can be optimized for a high spring constant with the first compression spring and for a space-saving construction with the second compression spring.

For example, the first compression spring can surround the driven member and the driven member can surround the second compression spring. The first compression spring can be disposed in the annular gap between the housing, in particular the inner sleeve, and a driven member. The second compression spring can be disposed in the annular gap between the rotation member and the driven member. Through this, it is possible to achieve a space-saving construction, at least for the region in which the second compression spring is disposed.

The intermediate element can extend through an elongated slot in the wall of the sleeve-shaped driven member that extends along the lengthwise axis. The slot can through this serve at the same time as a guide or as a lengthwise guide for the intermediate element on the driven member. The first spring can rest against the segment of the intermediate element that is outside the driven member, and the second compression spring can rest against the segment of the intermediate element that is within the driven member. The intermediate element is or will be movable or moved in the slot during the product discharge.

Generally preferably, the second compression spring is disposed distal to the first compression spring. In particular, the proximal end of the second compression spring can be disposed distal to the distal end of the first compression spring.

The second compression spring can preferably have a smaller outside diameter than the inner wall of the product container at which the piston of the product container lies movably. Because of the small outside diameter, an accidental contact of the compression spring can advantageously be avoided through a sufficient spacing from the inner wall.

The second compression spring can be disposed so that it is situated in the product container when the piston rod is moved to discharge the product in the product container. The intermediate element can be matched to the product container with regard to its position so that it is spaced from a proximal end of the product container along the lengthwise axis or contacts the proximal end of the product container when the maximum dischargeable amount of product has been discharged from the product container. If the intermediate element comes into contact with the distal end of the product container during product discharge, only the second compression spring can contribute to the discharge operation, which can be absolutely advantageous in special applications.

In a second sub-aspect, the driven member can have a shoulder, at which the at least one spring rests, in particular at its distal end. The at least one spring can be a single compression spring, i.e., a helical spring that acts as a compression spring. A segment of the driven member extending distal to the shoulder along the lengthwise axis can have a length, measured along the lengthwise axis, that is greater than the distance between the proximal end of the product container and the piston when the piston is in the position in which the maximally dischargeable amount of product in the product container has been discharged. In this embodiment the compression spring can be disposed only in the region proximal to the shoulder, and in the region distal to the shoulder, an additional spring need not be disposed. Through this, the region distal to the shoulder can be especially advantageously designed to be space saving.

In particular, the shoulder can have a non-rotatable and axially movable engagement with the housing. For example, the shoulder can firmly connect an inner sleeve of the driven member and an outer sleeve of the driven member, where the at least one compression spring can be or is disposed in the annular gap formed between the inner sleeve and the outer sleeve. For example, the outer sleeve can be in a non-rotatable and axially movable engagement with the housing, in particular the inner sleeve of the housing or the guide. This prevents rotation of the driven member relative to the housing, but allows movement along the lengthwise axis.

In a third sub-aspect, the at least one spring can be a torsion spring, in particular a helical spring wound from a strip material that rests against the rotation member and the abutment. Such a spring can be called a spiral or clock spring. The pretensioned torsion spring produces a torque between the rotation member and the abutment, where the torque attempts to rotate the rotation member relative to the abutment or the housing about the lengthwise axis. The torsion spring and preferably also the abutment for the torsion spring, at which the torsion spring rests, can be disposed distal to a dose display element and/or a bearing element that is movable along the lengthwise axis relative to the housing, the bearing element being in a threaded engagement with a dose display element. For the design of the dose display element and the bearing element, one is referred to the rest of the description of this application.

In the third sub-aspect, the rotation member can be connected to the driven member non-rotatably and axially movably. The rotation member can, for example, be sleeve-shaped and surround the driven member. The driven member and the rotation member can be connected so that the rotation member is non-rotatable and axially movable with respect to the driven member. The driven member can, for example, then be in a threaded engagement with the housing or an element fixed to the housing by means of its external thread. When the rotation member rotates, the driven member is screwed on the thread of the housing or the housing-affixed element along the lengthwise axis, due to which the product discharge, for example, can be undertaken, i.e., the piston in the product container can be moved in the distal direction.

Because the rotation member surrounds the driven member, the driven member can be designed in a rod shape, for example, in particular as a piston rod, through which it maintains a sufficient spacing from the inner wall of the product container when the driven member is moving in the product container.

Generally preferably, the angle of rotation of the rotation member can be proportional to the discharge stroke of the piston or the driven member. This can be achieved through the selective blocking or release of the rotation member.

Advantageously, the rotation member can be in an engagement, in particular a threaded engagement, with the driven member. Due to the thread pitch of the said threaded engagement, for example, with one complete rotation of the rotation member relative to the housing, the driven member can be shifted by the discharge spring by a stroke that corresponds to the thread pitch.

For example, the rotation member can have or be a threaded rod and the driven member can have or be a threaded nut, where the thread of the threaded nut engages the thread of the threaded rod.

In an alternative example, the rotation member can have or be a threaded nut and the driven member can have or be a threaded rod, where the thread of the threaded nut engages the thread of the threaded rod.

Preferably, the rotation member is axially fixed with respect to the housing or can be braced in an axially fixed way against the housing or an element affixed to the housing such as the abutment at least in one direction, preferably in the distal direction.

It is advantageous for the rotation member to be connected non-rotatably to the housing during the selection of a dose, i.e., in the unactuated state, in particular by means of the at least one coupling, in particular a first coupling, and to be rotated or to be rotatable relative to the housing during the actuation of the device for discharge of the product dose. The dose display element, in particular the dose display drum, can optionally be in a threaded engagement with the housing or an element affixed to the housing.

The dose display element, in particular the dose display drum, can be rotatable relative to the rotation member during the selection of a dose, i.e., in the unactuated state of the drive and dosing device or the actuation member. Preferably, the dose display element is non-rotatable and, for example, axially movable relative to the rotation member during the actuation of the device for discharge of the product dose, or is connected non-rotatably with the rotation member, in particular with the at least one coupling, in particular a second coupling.

Advantageously, during the dose discharge, i.e., during the actuation of the actuation member, the discharge spring screws the dose indicator element back to its null position, in particular via the rotation member and preferably via a coupling member, which is preferably disposed non-rotatably, but axially movably, in reference to the dose indicator element. In particular, the coupling member and the dose indicator element can be in a non-rotatable engagement, which allows an axial movement between the dose indicator element and the coupling member. The engagement can be produced, for example, by means of a lengthwise guide. Preferably, the coupling member is connected axially fixed but rotatable to the bearing element.

The first coupling can be operably connected between the housing, in particular the bearing element, and the rotation member. The first coupling is coupled during the selection of the product dose or when the actuation member is unactuated, so that the rotation member is non-rotatable relative to the housing. During the product discharge or with the actuation member actuated, the first coupling is uncoupled, so that the rotation member can be rotated relative to the housing.

The first coupling can have a first coupling structure, which is connected non-rotatably to the housing, in particular is formed by the housing or the bearing element, and a second coupling structure, which is connected non-rotatably to the rotation member, in particular is formed by the rotation member. The first coupling structure can have or be a gear structure, where the second coupling structure can have or be a gear structure. The gear structures of the first coupling structure and the second coupling structure can mesh positively when the first coupling is coupled. The first coupling structure can be an external gear structure, and the second coupling structure can be an internal gear structure. Alternatively, the first coupling structure can be an internal gear structure, and the second coupling structure can be an external gear structure.

The second coupling can be disposed between a sleeve-shaped coupling member, which is, for example, connected rotatably and axially fixed to the bearing element, in particular can mesh with it, and the rotation member. The second coupling is uncoupled during the selection of the product dose or when the actuation member is unactuated, so that the coupling member is able to rotate relative to the rotation member. The second coupling is coupled during the product discharge or with the actuation member actuated. Through this, in particular the rotation member and the coupling member are non-rotatably connected. The coupling member can thus be rotated by the rotation member. The second coupling can comprise a third coupling structure, which is connected non-rotatably to the coupling member, in particular is formed by the coupling member, and a fourth coupling structure, which is connected non-rotatably to the rotation member, in particular is formed by the rotation member. The third coupling structure can have or be a gear structure, and the fourth coupling structure can have or be a gear structure. The gear structures of the third and fourth coupling structures can mesh positively, when the second coupling is coupled. For example, the third coupling structure can be an internal gear structure, where the fourth coupling structure can be an external gear structure. Alternatively, the third coupling structure can be an external gear structure and the fourth coupling structure can be an internal gear structure.

Basically, the gear structures for the second coupling structure and the fourth coupling structure can be gear structures that are separate from each other. Preferably, the second coupling structure and the fourth coupling structure are formed by a common gear structure.

In particular, the first and the second couplings can be matched to each other so that the actuation member can take an intermediate position, for example a first intermediate position, between the unactuated position and the actuated position, an intermediate position in which the first coupling is coupled and the second coupling is coupled. This advantageously results in the rotation of the coupling member by the drive spring only being released when it is ensured that the rotation member is coupled non-rotatably to the coupling member. This advantageously avoids an erroneous operation of the device that could arise if the second coupling were not yet coupled and the first coupling were already uncoupled.

The drive and dosing device preferably has a third coupling, which is disposed between the dose selection element and the coupling member. The third coupling is coupled during the selection of the product dose or with the actuation member unactuated, so that the coupling member and the dose selection element are fixed non-rotatably with respect to each other. During the product discharge or with the actuation member actuated the third coupling is uncoupled, so that the coupling member is rotatable relative to the dose selection element by means of the pretensioned drive spring.

The third coupling can have a fifth coupling structure, which is non-rotatably connected to the dose selection element, in particular is formed by the dose selection element, and a sixth coupling structure, which is non-rotatably connected to the coupling member, in particular is formed by the coupling member. The fifth coupling structure can be or have a gear structure, and the sixth coupling structure can be or have a gear structure. The gear structures of the fifth coupling structure and the sixth coupling structure can intermesh positively if the third coupling is coupled. The fifth coupling structure can be an internal gear structure, and the sixth coupling structure can be an external gear structure. Alternatively, the fifth coupling structure can be an external gear structure, and the sixth coupling structure can be an internal gear structure.

In particular, the first and the third couplings can be matched to each other so that the actuation member can take an intermediate position between the unactuated position and the actuated position, for example a second intermediate position, in which the first coupling is coupled and the third coupling is coupled.

Preferably, the drive and dosing device can have a fourth coupling, which is disposed between, in particular operably connected between, the dose selection element and the housing. The fourth coupling is uncoupled during the selection of the product dose or when the actuation member is unactuated, so that the dose selection element is rotatable relative to the housing. During product discharge or with the actuation member actuated, the fourth coupling is coupled, so that the dose selection element is non-rotatable relative to the housing. It is generally preferable for the dose selection element to be non-rotatable relative to the housing during product discharge.

The third coupling can have a seventh coupling structure, which is non-rotatably connected to the housing, in particular is formed by the housing, and an eighth coupling structure, which is non-rotatably connected to the dose selection element, in particular is formed by the dose selection element or the actuation member, which can, for example, be connected permanently non-rotatably to the dose selection element. The seventh coupling structure can be or have a gear structure, and the eighth coupling structure can be or have a gear structure. The gear structures of the seventh coupling structure and the eighth coupling structure can intermesh positively when the third coupling is coupled. The seventh coupling structure can be an external gear structure, and the eighth coupling structure can be an internal gear structure. Alternatively, the seventh coupling structure can be an internal gear structure, and the eighth coupling structure can be an external gear structure.

In generally preferred embodiments, the dose display element can have a stop, for example a zero dose stop, which is moved away from a counterstop, in particular a zero dose counterstop, when a dose increase is made, and which is moved toward the counterstop when a dose reduction is made, or when the device is actuated for discharge of the selected product dose.

In particular, the dose display element can be at least rotationally uncoupled from the rotation member during the selection of the product dose, i.e., when increasing and decreasing the dose, and coupled to the rotation member during the actuation of the device for discharge of the product dose so that a rotation of the rotation member causes the dose display element to be moved toward the counterstop, i.e., the zero dose stop moves toward the zero dose counterstop. If the zero dose stop and the zero dose counterstop are at a stop or in contact, this and in particular the second coupling will prevent rotation of the rotation member and thus a further advance of the driven member relative to the housing.

In advantageous further developments the drive and dosing device can have a mechanism to prevent the selection of a dose that exceeds the amount of a medication in the product container. In particular, the said mechanism can block the rotation of the dosing member in a direction that would cause a dose increase, especially if the maximum dose stop of the dose display element and the maximum dose counterstop are not yet in engagement or if a dose is shown in the indicator device that is less than the maximum selectable product dose. The mechanism thus prevents the selection of a dose that exceeds the residual amount of the product contained in the product container, so that the danger of possible misuse of the drive and dosing device is reduced. The mechanism can, for example, have a limiter that is brought between two parts, of which one rotates relative to the other during dose selection and does not rotate during actuation, i.e., dose discharge. For example, the limiter can be disposed between the dose selection element, which can be designed in particular as a dose selection button or dose selection sleeve, and the housing or an element affixed to the housing. The limiter, the dose selection element, and the housing can be coupled to each other so that a relative rotation, especially during dose selection, between the dose selection element and the housing causes the limiter to move to a stop position, in which the limiter prevents the selection of a dose that exceeds the amount of a product in the product container. Examples of correspondingly suitable limiters are disclosed in WO 2010/149209 or in WO 01/19434 A1, in particular in FIG. 3 therein. For example, the limiter can have an internal thread, which is in engagement with an external thread on the housing. In particular, the limiter can have a lengthwise guide on its outer side, with which it engages with the dose selection element so that the dose selection element is non-rotatable relative to the limiter. Alternatively, the housing can have the lengthwise guide for the limiter, so that the limiter is non-rotatable relative to the housing, and the limiter can have a thread, in particular an external thread, which meshes with the thread, in particular an internal thread of the dose selection element.

The stop position is defined by a stop for the limiter, and the stop can be formed by the housing or the dose selection element or by a means that is fixed to the housing at least axially or in the circumferential direction. If the limiter and the stop are in contact, a rotation of the dose selection element in a direction of rotation that would cause an increase of the dose is no longer possible or is blocked.

In generally preferred further developments, in particular of the first and second aspect, the drive and dosing device can have at least one signal generating mechanism that is designed to generate an acoustic and/or tactile signal, in particular by mechanical means, during the dose selection and/or the product discharge. Such a signal can be perceived in particular as a click signal. For example, there can be a (first) signal generation mechanism that generates the signal during the dose selection and optionally can be called a dose clicker device. Furthermore, there can be another (second) signal generation mechanism, which generates the signal during the product discharge and can optionally be called a discharge clicker device. Alternatively, there can be a (common) signal generation mechanism that generates the signal during the dose selection and during the product discharge.

The dose clicker device can in general be disposed between two parts that move, in particular rotate, relative to each other during dose selection and/or product discharge. One of the parts can be a springy snap element, for example, which meshes in a gear structure of the other of the two parts, which is disposed over the circumference, for example. If one part rotates relative to the other, the snap element can move over the gear structure and thereby generate the signal. The gear structure can be formed by an inner circumference or an outer circumference or a face surface of the part.

The dose clicker device for the dose selection can be formed in particular between the coupling member and the bearing element or rotation member. Preferably, during dose selection, the coupling member rotates relative to the bearing element or the rotation member, so that the signal generation mechanism that generates the signal during dose selection is formed. The coupling member can form the snap element and the rotation member or the bearing element can form the gear structure in which the snap element meshes. The gear structure can, for example, be the gear structure that forms the second and/or fourth coupling structure.

The discharge clicker device for the product discharge can be formed in particular between the coupling member and the actuation member. For example, the actuation member can form the gear structure, in particular an internal gear structure, and the coupling member or a clicker connected non-rotatably to the coupling member can form the snap element. Preferably, the coupling member rotates relative to the actuation member or the dosing member during, especially only during, the product discharge, so that the signal generation mechanism is formed that generates the signal during the product discharge.

BRIEF DESCRIPTION OF THE DRAWINGS

FIGS. 3A-D show various representations of a third embodiment of a drive and dosing device in accordance with the invention, FIGS. 4A-D show various representations of a fourth embodiment of a drive and dosing device in accordance with the invention,

DETAILED DESCRIPTION

Figures 1A, 1B, 1C, 1D:
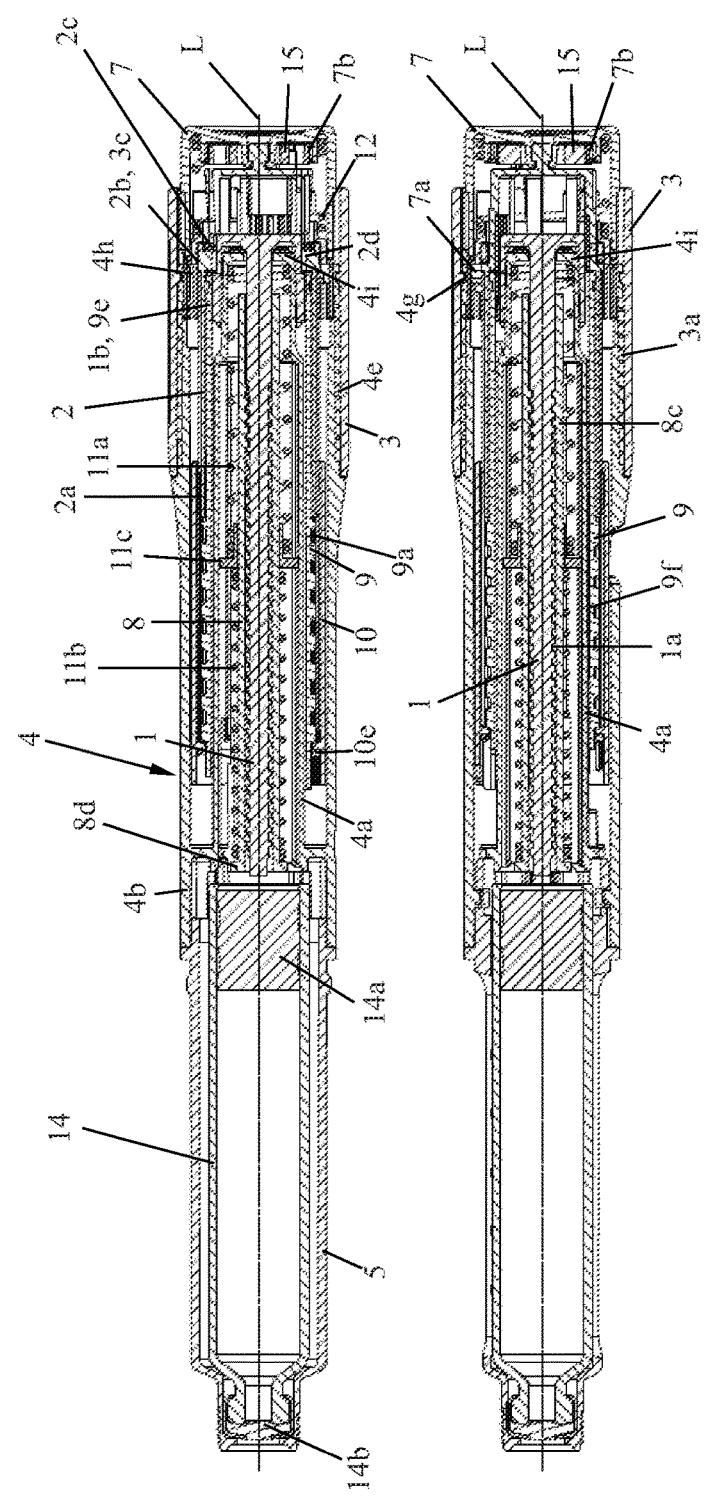
FIGS. 1A-D show various representations of a first embodiment of a drive and dosing device in accordance with the invention.

According to the first to fourth embodiments, the drive and dosing device comprises a sleeve-shaped housing 4, which has an outer sleeve 4b, which can be held by the user by hand. The housing 4 further comprises an inner sleeve 4a, which forms an abutment 4i and is disposed concentrically to the outer sleeve 4b. Inner sleeve 4a and outer sleeve 4b are connected to each other via an annular projection. An annular gap is formed between the outer sleeve 4b and the inner sleeve 4a; a dose display element 10, which is designed in particular as a dose display drum, i.e., is made sleeve-shaped, a bearing element 9, and a coupling member 2, which is sleeve-shaped and can in particular also be called the indicator coupling, are disposed in the annular gap of the housing 4.

At the distal end of the housing 4, there is a sleeve-shaped product holder receptacle 5, preferably of a transparent material, in which a product container 14 in the form of a cartridge is accommodated. The product holder 14 is inseparably connected to the housing 4 by means of the product holder receptacle 5 so that the drive and dosing device, in particular together with the product holder receptacle 5 and the product holder 14, forms a one-way injection device, which can be discarded in its entirety after the product container 14 has been completely emptied. The product holder 14 has a septum 14b at its distal end, which can be punctured by a needle mounted at the distal end of the product container 14 or the product container receptacle 5. A piston 14a is accommodated in the product container 14, and the product to be discharged is disposed between the septum 14b and the piston 14a. A moving of the piston 14a in the direction of the septum or in the distal direction, thus the discharge direction, causes a discharge of the product contained in product container 14. There can be a protective cap (not shown) provided, which can be placed over the product holder receptacle 5 and removed before the injection of a dose.

The drive and dosing device has a driven member 8 and a rotation member 1. The driven member 8 is disposed so that a distal end 8d acts on the piston 14a, in particular can press against the piston 14a. The rotation member 1 is disposed axially fixed relative to the housing 4 and rotatable about the lengthwise axis L. The rotation member 1 and the driven member 8 are coupled together or they intermesh so that a rotation of the rotation member 1 relative to the housing 4 and/or to the driven member 8 causes a movement of the driven member 8 along the lengthwise axis L in the distal direction for moving the piston 14a.

The rotation member 1 has, at its proximal end, an increased diameter, in particular in the form of a widened head. Teeth forming an external gear structure are disposed parallel to the lengthwise axis L on the head, the teeth serving as the second and/or fourth coupling structure 1b, as described below. A ring-shaped friction surface that is smaller in diameter than the head is disposed on the head and is in contact with an annular projection of the housing 4 that projects inwardly, for example forming an abutment 4i. Through the reduced diameter of the ring-shaped friction surface the point of attack of the resulting force is moved closer to the lengthwise axis L, so that the frictional torque between the rotation member 1 and the housing 4 is reduced.

The drive and dosing device according to the first to fourth embodiments has at least one discharge spring 11; 11a, 11b. The at least one discharge spring 11; 11a, 11b as supplied, i.e., in the delivered state of the drive and dosing device, is pretensioned enough that the energy stored in it is sufficient to discharge essentially completely the product contained in the product holder 14, in particular in a plurality of individual discharges, between which a new dose selection is made each time. The advantage of the at least one pretensioned spring 11; 11a, 11b is that the at least one spring 11; 11a, 11b does not, for example, have to be tensioned during the dose selection, so that an energy-saving, i.e., easier, dose selection can be undertaken by the user of the device.

In the first to third embodiments, the at least one discharge spring 11; 11a, 11b is made as a helical or coil spring, which acts as a compression spring and accordingly strives to push the abutment 4i and the driven member 8 away from each other, i.e., to move the driven member 8 in the distal direction relative to the housing 4.

The housing 4, in particular the inner sleeve 4a and a sleeve-shaped driven member 8, which can also be called a ram, are coupled non-rotatably and axially movably relative to each other. The driven member 8 is non-rotatable relative to the housing and axially movable along the lengthwise axis L.

The rotation member 1 is designed as a threaded rod, which forms an external thread 1a and is in a threaded engagement with an internal thread of the sleeve-shaped driven member 8. The pitch of the thread of the threaded engagement between the driven member 8 and the rotation member 1 is great enough that a self-locking effect does not arise in the threaded engagement, i.e., the rotation member 1 is rotatable or can be turned relative to the driven member 8 about the lengthwise axis L because of the axial force of the discharge spring 11 acting along the lengthwise axis L.

The housing 4, in particular the proximal end of the inner sleeve 4a, forms the abutment 4i for the at least one discharge spring 11; 11a, 11b, which rests against the abutment 4i and the region of the distal end of the driven member 8. The at least one spring 11; 11a, 11b is a single spring in the third embodiment (FIGS. 3A-3D) and a first spring 11a and a second spring 11b in the first and second embodiments (FIGS. 1A-1D and 2A-2D). The first spring 11a and the second spring 11b are connected in series.

In the third embodiment (FIGS. 3A-3D), the distal end of spring 11 rests against an annular projection, in particular the shoulder 8g of the driven member 8, which solidly connects an outer sleeve and an inner sleeve 8b of the driven member 8. The proximal end of spring 11 rests against the annular projection that forms the abutment 4i, which is formed by housing 4 and projects inwardly. Spring 11 is at least partially disposed in the annular gap between the outer sleeve and the inner sleeve 8b of the driven member 8. The inner sleeve 8b of the driven member 8 has the internal thread 8c for threaded engagement with the rotation member 1. The driven member 8, in particular its outer sleeve, and the housing 4, in particular its inner sleeve 4a, intermesh so that the driven member 8 is non-rotatable about the lengthwise axis L relative to the housing 4 and is movable along the lengthwise axis L. A guide is formed between the inner sleeve 4a and the driven member 8 or its outer sleeve by means of at least one lengthwise rib 8a and at least one lengthwise guide 4c, which prevents rotation of the driven member 8 relative to the housing 4 and allows axial movement of the driven member 8 relative to the housing 4. The lengthwise rib 8a is preferably formed by the outer sleeve of the driven member 8. The driven member 8 has the inner sleeve 8b, which in this example has at its proximal end the internal thread 8a, which meshes with the external thread 1a of the rotation member 1, which is designed as a threaded rod.

The annular projection, in particular shoulder 8g, of the driven member 8 is disposed in the proximal half, in particular in the proximal third, of the driven member 8, with respect to the total length of the driven member 8 measured along the lengthwise axis L. The distance between the distal end of the driven member 8 and the annular projection of the driven member 8, measured along the lengthwise axis L, is preferably greater than the distance between the piston 14a and the proximal end of the product container 14, measured along the lengthwise axis L, when the piston 14a is in the position in which the maximum amount of product that can be discharged from the product container has been discharged, i.e., when the product container has been essentially completely emptied. This advantageously keeps the annular projection from bumping against the proximal end of the product container 14 or at least moving in the product container 14.

Figure 5:
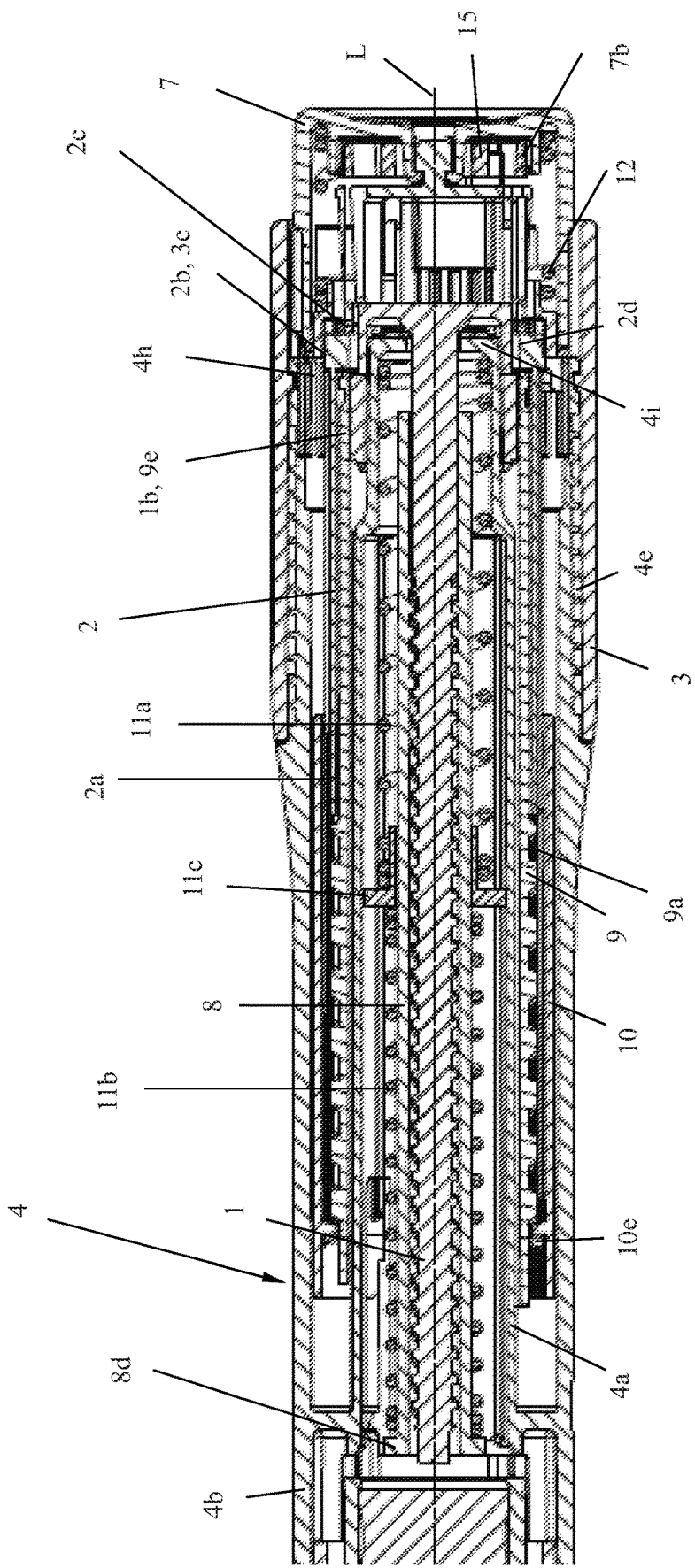
FIG. 5 shows an enlarged view of FIG. 1C, FIGS. 2A-D show various representations of a second embodiment of a drive and dosing device in accordance with the invention.

In the first and second embodiments (FIGS. 1A-1D and 2A-2D and 5), the proximal end of the first spring 11 rests against the inwardly projecting annular projection formed by the housing 4, which forms the abutment 4i. The distal end of spring 11 rests against an intermediate element 11c, which is in particular ring-shaped and preferably surrounds the driven member 8. The distal end of the second spring 11b rests against an annular projection or annular collar, for example in the region of the distal end 8d of the driven member 8. The proximal end of the second spring 11b rests against the intermediate element 11c. The intermediate element 11c couples the driven member 8 and the housing 4 so that the driven member 8 is movable along the lengthwise axis L relative to housing 4 and is non-rotatable about the lengthwise axis L. The intermediate element 11c and the inner sleeve 4a of the housing 4 intermesh so that the intermediate element 11c is non-rotatable and axially movable with respect to housing 4. The intermediate element 11c and the driven member 8 intermesh so that the intermediate element 11c is movable along the lengthwise axis L relative to the driven member 8 and is non-rotatable about the lengthwise axis L.

The second spring 11b has an outside diameter that is less than the inside diameter of the first spring 11a. Through this, it can be ensured that the region of the driven member 8 or the first spring 11b, which is moved in the product container 14 for product discharge, has sufficient spacing from the inner wall of the product container 14 that guides the piston 14a. The proximal end of the second spring 11b is disposed distal to the distal end of the first spring 11a.

The intermediate element 11c is disposed so that it is at a distance along the lengthwise axis L from a proximal end of the product container 14 when the maximum dischargeable amount of product has been discharged from the product container 14, i.e., when the product container 14 has been essentially completely emptied. This ensures that the first and the second springs 11a and 11b participate in the discharge process until the product discharge is complete.

In the first embodiment, the first spring 11a surrounds the driven member 8, and the second spring 11b surrounds the driven member 8. In other words, the first spring 11a and the second spring 11b are disposed in the annular gap formed between the driven member 8 and the inner sleeve 4a of the housing 4. This arrangement allows a particularly simple assembly of the drive and dosing device.

In the second embodiment (FIGS. 2A-2D), the first spring 11a surrounds the driven member 8, and the driven member 8 surrounds the second spring 11b. In other words, the first spring 11a is disposed in the annular gap between the inner sleeve 4a and the driven member 8. The second spring 11b is disposed in the annular gap formed between the rotation member 1 and the driven member 8. The sleeve-shaped driven member 8 has at least one lengthwise slot 8f that extends parallel to the lengthwise axis L, through which the intermediate element 11c engages and in which the intermediate element 11c is movable. Advantageously, the first spring 11a and the second spring 11b can rest against the intermediate element 11c. The slot 8f can advantageously provide for the non-rotatable and axially movable engagement of the intermediate element 11c with the driven member 8.

In the fourth embodiment, which is shown in FIGS. 4A-4B, the rotation member 1 is sleeve-shaped and surrounds the elongated driven member 8, which is made in particular as a threaded rod. The driven member 8 and the rotation member 1 intermesh so that the driven member 8 is, with respect to the rotation member 1, non-rotatable about the lengthwise axis L and is movable along the lengthwise axis L. The driven member 8 has an external thread, which is in threaded engagement with an internal thread of the housing 4. A rotation of the rotation member 1 relative to the housing 4 causes a rotation of the driven member 8, so that the driven member 8 screws along the lengthwise axis L at the housing 4.

Spring 11 in the fourth embodiment is a spring that is helically wound from a strip material and serves as a torsion or rotational spring. Such springs are also called clock springs.

One end of spring 11 rests against the rotation member 1 and the other end rests against the housing 4 or the housing-fixed housing insert that forms the inner sleeve 4a. The inner sleeve 4a is connected to housing 4 or the external sleeve 4b via an annular projection, where the spring 11 is disposed distal to the annular projection. Spring 11 is in particular disposed distal to a dose display element 10 and/or a bearing element 9. The bearing element 9 and/or the dose display element 10 are disposed proximal to the annular projection. Spring 11 is disposed between the annular projection that connects the inner sleeve 4a to the outer sleeve 4b and the annular projection that has the internal thread for the threaded engagement with the driven member 8. This arrangement especially advantageously allows the torque generated by spring 11 to be transmitted to the driven member 8 over the shortest possible path during product discharge.

Especially preferably, the outside diameter of spring 11 is greater than the inside diameter of the sleeve-shaped segment 4a.

We now refer again in general to the first to fourth embodiments. By rotation of the rotation member 1 relative to the housing 4 and the driven member 8, the spring 11 can move the driven member 8 in the distal direction over a discharge stroke that is proportional to the angle of rotation of the rotation member 1. By selective blocking and releasing of the rotation member 1, which can be brought about by actuating an actuation member 7 that is designed as an actuation button, the movement of the driven member 8 relative to the housing 4, i.e., the discharge stroke of the driven member 8, can be controlled.

The drive and dosing device further has a bearing element 9, which can be called the indicator drum bearing element, and is disposed non-rotatable relative to housing 4 but movable along the lengthwise axis L. The bearing element 9 is sleeve-shaped and preferably surrounds the inner sleeve 4a of housing 4, where in particular the outer sleeve 4b surrounds the bearing element 9. The bearing element 9 is in engagement with the housing 4, in particular the inner sleeve 4a, which allows lengthwise movement of the bearing element 9 relative to housing 4, but prevents rotary motion. The engagement can be formed by a lengthwise guide 9f between the bearing element 9 and the inner sleeve 4a.

The bearing element 9 has a thread 9a, in particular an external thread, in which a thread 10e, in particular an internal thread, of the dose display element 10 engages. Through the said threaded engagement, the display element 10 can be screwed relative to the bearing element 9.

These embodiments comprise a signal generation mechanism for dose selection (dose clicker device) and a signal generation mechanism for the product discharge (discharge clicker device), which generate in each case an acoustic and/or tactile signal during dose selection or product discharge.

The discharge clicker device has a ring-shaped clicker 15, which is disposed in the actuation member 7 and has a snap element, which engages in a springy or elastically bending way in an internal gear structure 7b of the actuation member 7 that extends over the circumference. The clicker 15 and the coupling member 2 are engaged non-rotatably about the lengthwise axis L, so that the clicker 15 is also turned by the coupling member 2 when the coupling member 2 is rotated about the lengthwise axis L relative to the housing 4. A rotation of the sleeve-shaped coupling member 2 relative to housing 4 and/or actuation member 7 causes the snap element of the clicker 15 to snap over the internal gear structure 7b and in this way generate the acoustic and/or tactile signal.

The dose clicker device has a springy engagement element at the coupling member 2, which meshes in the external gear structure that forms the second coupling structure 1b. The coupling member 2 rotates relative to the rotation member 1 during dose selection, so that the snap element 2c snaps over the second coupling structure 1b and in doing so generates the acoustic and/or tactile signal during dose selection. The external gear structure, in particular the spacing between the teeth, is designed so that it allows the selection of discrete dose-proportional angular steps and/or the generation of a slight resistance in dose selection and/or the generation of the acoustic or tactile signal, for example an audible or palpable click, during dose selection.

The dose display element 10 is connected to the coupling member 2 non-rotatably, but axially movably, in particular in engagement. The engagement comprises a lengthwise guide 2a, which causes the dose display element 10 to be non-rotatable with respect to the coupling member 2, but axially movable. A rotation of the coupling member 2 relative to the bearing element 9, because of the non-rotatable connection between coupling member 2 and dose display element 10, causes the dose display element 10 to rotate as well and, because of the threaded engagement of thread 10e with the thread 9a of the dose display element 9, to be screwed along at the bearing element 9, in particular in addition to the clicking noise generated because of the snap members.

Over its external circumference, the dose display element 10 has a dose scale extending in a spiral in correspondence with the pitch of the thread 10e, the scale comprising a plurality of successive scale values. In the indicated example, a maximum dosage of 80 IU can be selected with the drive and dosing device, and the scale runs from 0 to 80 and the dose values are given in steps of two.

The dose display element 10 has, for example at its proximal end, a stop surface pointing and acting in the circumferential direction, which is called the zero dose stop. The dose display element 10 has, for example at its distal end, which is opposite to the proximal end, a stop surface acting and pointing in the circumferential direction, which is called the maximum dose stop.

The dose display element 10 can be screwed back and forth between a zero dose position and a maximum dose position at the bearing element 9. In the zero dose position, the zero dose stop, in combination with a zero dose counterstop formed by the housing 4, prevents the rotation of the dose display element 10 in a first direction of rotation, namely a direction of rotation that would cause a dose smaller than zero to be selected. In the zero dose position, the dose display element 10 can be turned in the opposite, i.e., second direction of rotation.

In the maximum dose position, the maximum dose stop, in combination with a maximum dose counterstop, which is formed by the bearing element 9, prevents the rotation of the dose display element 10 in the second direction of rotation, which would cause an increase of the dose beyond the maximum selectable value. Rotation in the first direction of rotation is possible in the maximum dose position. Although the maximum dose counterstop is formed by the bearing element 9, in a departure from this example, the maximum dose counterstop can optionally be formed by the housing 4. The zero dose counterstop can, in a departure from the said example, be formed by the bearing element 9.

The housing 4 has an indicator device 4d in the form of a window, which provides a clear view of the scale of the dose display element 10. A dosing member 3 in the form of a dosing button is mounted rotatably but axially fixed on housing 4. For this, the housing 4 has an annular groove 4g, in which in particular an annular shoulder of the dosing member 3 meshes. The dosing member 3 has a gripping structure 3b over its outer surface, which makes it easier for the user of the device to rotate the dosing member 3 relative to housing 4. In an unactuated state of the device, a rotation of the dosing member 3 produces a rotation or screwing movement of the dose display element 10, so that the desired dose is selectable and can be read in the indicator device 4d.

An actuation member 7 in the form of an actuation button, which is movable relative to the dosing member 3 for an actuation of the device for a product discharge, in particular along the lengthwise axis L, is disposed at the dosing member 3. The actuation member 7 forms the proximal end of the device and is easily actuated by the thumb of the hand of the user that holds the housing 4, in particular is movable relative to the housing 4 and/or the dosing member 3. The coupling member 2 is rotatable and axially fixed relative to the actuation member 7, in particular when the dosing coupling 2b, 3c is released. Preferably, the actuation member 7 is attached to the coupling member 2 in an axially fixed but rotatable way.

The drive and dosing device further has a reset or coupling spring 12, which is tensioned upon actuation of, in particular pressing, the actuation member 7 and which resets the bearing element 9 and/or the actuation member 7 to its unactuated position when the actuation member 7 is unactuated. An actuation of the actuation member 7 causes, in addition to its axial movement, the axial movement of the bearing element 9 along the lengthwise axis L. The spring 12 rests against the dosing member 3 at its distal end and at the actuation member 7 at its proximal end. The spring 12 is preferably a helical or spiral spring that acts as a compression spring.

The dosing member 3 is non-rotatable relative to the actuation member 7. The actuation member 7 engages an inwardly projecting shoulder of the dosing member 3. At the distal end of the preferably pot-shaped actuation member 7, there is an eighth coupling structure 7a in the form of an external gear structure, which becomes coupled with a seventh coupling structure 4h formed on the housing 4 in the form of an internal gear structure, in particular at the proximal end of the housing 4, through actuation of the actuation member 7, so that the dosing member 3 is non-rotatable with respect to the housing 4. Because of this, when the device is actuated, a dose selection, i.e., a rotation of the dosing member 3 relative to the housing 4, is not possible, but becomes possible only when the actuation member 7 is unactuated. The seventh and eighth coupling structures 4h and 7a form a fourth coupling 4h, 7a.

A third coupling 2b, 3c is formed between the dosing member 3 and the coupling member 2. The dosing member 3 forms a sixth coupling structure 3c of the third coupling 2b, 3c, in particular at the inward projecting shoulder. When the actuation member 7 is unactuated, the sixth coupling structure 3c is non-rotatably coupled with a fifth coupling structure 2b of the third coupling 2b, 3c, which is formed as an external gear structure on coupling member 2. In the unactuated state of the actuation member 7, the third coupling 2b, 3c is coupled. The third coupling 2b, 3c can also be called the dosing coupling, which is coupled during dose selection, i.e., with the actuation member 7 unactuated, and is uncoupled during a dose discharge, i.e., when the coupling member 7 is actuated, and the third coupling 2b, 3 transmits a torque in the coupled state and does not transmit torque in the uncoupled state. The third coupling 2b, 3c is uncoupled by a sliding of the coupling member 2 relative to the housing 4, in particular due to actuation of the actuation member 7.

The bearing element 9 has at its proximal end on the inner circumference a first coupling structure 9e, which is formed by an inner gear structure disposed over the circumference, which is in engagement with the gear structure of the rotation member 1 that forms the second coupling structure 1*b*, in particular when the actuation member 7 is unactuated. The first coupling structure 9*e* and the second coupling structure 1*b* form a first coupling 1*b*, 9*e*. When the coupling structure 9*e*, 1*b* interlocks, i.e., the coupling 1*b*, 9*e* is coupled, the rotation member 1 is non-rotatable with respect to the housing 4. The coupling member 2 further has a third coupling structure 2*d* on an internal circumference, which has an internal gear structure disposed over the circumference. The third coupling structure 2*d* is disposed so that when the actuation member 7 is actuated, it comes into a non-rotatable engagement with the rotation member 1, in particular with the coupling structure 1*b* or alternatively one of the two coupling structures 1*b* of the fourth coupling structure, which is separate, but not shown in this example. The third coupling structure 2*b* and the second or fourth coupling structure 1*b* form a second coupling 1*b*, 2*d*.

While the actuation member 7 is being moved along the lengthwise axis L relative to the dosing member 3 for the actuation, the second coupling 1*b*, 2*d* is additionally being coupled. By further sliding of the actuation member 7 relative to the dosing member 3, the first coupling 1*b*, 9*e* becomes coupled. Before, after, or at the same time as the uncoupling of the first coupling 1*b*, 9*e* the third coupling 2*b*, 3*c* becomes uncoupled, and/or the fourth coupling 4*h*, 7*a* becomes coupled.

In particular because the first coupling structure 9*e* is separated from the second coupling structure 1*b*, the at least one discharge spring 11; 11*a*, 11*b* can slacken, where the rotation member 1 is rotated relative to the housing 4 and, because of the engagement of the second coupling structure 1*b* with the third coupling structure 2*d*, the coupling member 2 and thus also the dose display element 10 are rotated relative to the housing 4, so that the dose display element 10 is screwed back to its zero dose position and the driven member 8 is moved in the distal direction in proportion to the spacing extended in particular in the circumferential direction between the zero dose stop 10*c* and the zero dose counterstop 4*f* over a discharge stroke relative to the housing 4 in the distal direction. The rotation of the coupling member 2 relative to the actuation member 7 causes the snap element of the clicker 15 to snap over the gear structure 7*b*, in particular in dose-proportional angular steps, and thus to generate the acoustic and/or tactile signal.

The drive and dosing device has a dose limiter in the form of a ring, a ring segment, or a nut, which has a thread on its internal circumference, which meshes into a thread 4*e* disposed on an external circumference of the housing 4, so that the dose limiter can be screwed relative to the housing 4. On the external circumference, the dose limiter has an engagement member, which meshes into a lengthwise guide 3*a* on the inner circumference of the dosing member 3, so that the dose limiter is non-rotatable relative to the dosing member 3, but is axially movable. A stop is formed at the dosing member 3 or the housing 4, and the dose limiter is spaced from the stop in proportion to the maximum amount of product that can be discharged from the product container 14. Since during dose selection the dosing member 3 turns relative to the housing 4 and does not turn during a dose discharge, a counter that sums the already discharged individual doses and the currently selected dose and accordingly continuously moves closer to the stop of the dosing member 3 or the housing 4 can be formed via the dose limiter. An increase of dose causes the dose limiter to move toward the stop. A dose reduction causes the dose limiter to move away from the stop. If the remaining dose in the product container 14 is less than the maximum dose that can be selected with the drive and dosing device, the dose limiter comes into contact with the stop, so that an erroneous rotation of the dosing member 3 relative to the housing 4 in a direction of rotation that would have an increase of the dose as a result becomes blocked.

The system of first coupling 1*b*, 9*e* and second coupling 1*b*, 2*d* can also be called the discharge coupling.

In FIGS. 1A-1D, 2A-2D, and 3A-3D, the drive and dosing device, which can also be called an injection device, is shown in its starting or as-delivered state, in particular before a first use. The product dose may be displayed in the indicator device 4*d* as 0. An actuation of the actuation member 7 has the result that no dose is discharged. The dose limiter has a distance to the stop that is proportional to the amount of product that is contained in the product container 14 or that is dischargeable from it, for example 300 IU.

To select the product dose, the dose selection member 3 is rotated relative to the housing 4, so that, due to the coupled third coupling 2*b*, 3*c*, the coupling member 2 and thus also the dose display element 10 are rotated relative to the housing 4. In doing so, the dose display element 10 is screwed along the bearing element 9 because of the threaded engagement of the thread 10*e* with the thread 9*a*. In particular, the spacing between the zero dose stop and the zero dose counterstop becomes increased in proportion to the dose indicated in the indicator device 4*d*. In addition, during the rotation an audible and palpable signal is generated because of the snapping of the snap member over the gear structure 1*b*.

If a maximum selectable dose was selected, for example 80 IU, which then can be read in the indicator device 4*d*, a further increase of dose is not possible because of the interaction, in particular the contact of the maximum dose stop with the maximum dose counterstop. The dose limiter is moved closer or moved to the stop in correspondence with 80 IU.

To discharge the selected or displayed dose, the actuation member 7 is actuated, in particular pressed, i.e., moved in the distal direction relative to the housing 4 and the housing member 3, so that the coupling member 2 and the bearing element 9 as well as the dose display element 10 are moved in the distal direction relative to the housing 4, in particular against the force of the coupling or reset spring 12.

The actuation of the actuation member 7 causes the second coupling 1*b*, 2*d* to be coupled and the first coupling 1*b*, 9*e* to be uncoupled, so that the rotation member 1 is no longer non-rotatable, but rather is rotatable with respect to housing 4 and is non-rotatable with respect to the coupling member 2 and the dose display element 10. The actuation of the actuation member 7 additionally causes the third coupling 2*b*, 3*c* to become uncoupled and the fourth coupling 4*h*, 7*a* to be coupled. In the actuated state of the actuation member 7, the rotation member 1 is non-rotatable relative to the dose display element 10, so that the rotation member 1 and the dose display element 10 can rotate together relative to the housing 4. Through the force of the energy stored in the at least one discharge spring 11; 11*a*, 11*b* on the driven member 8 and because of the threaded engagement of the driven member 8 with the rotation member 1, a rotation of the rotation member 1 and the dose display element 10 relative to the housing 4 is brought about, so that the dose display element 10 on the bearing element 9 is screwed back in the direction of the zero dose position and the dose displayed in the indicator device 4*d* counts down. At the same time, the driven member 8 is moved in the distal direction relative to the housing 4 by the discharge stroke by the at least one discharge spring 11; 11a, 11b, the discharge stroke being proportional to the previously selected dose. When the dose display element 10 has reached its zero dose position, discharge of the previously selected dose or single dose is complete. If the user releases the actuation member 7, the coupling or reset spring 12 returns the actuation member 7, the coupling member 2, the bearing element 9, and the dose display element 10 back. Upon resetting, the said elements are moved in the proximal direction relative to the housing 4 or the dosing member 3.

When the device is reset by spring 12, the first coupling 1b, 9e becomes coupled and the second coupling 1b, 2d becomes uncoupled. The rotation member 1 is now again non-rotatable with respect to the housing 4, and the dosing member 3 together with the dose display element 10 are rotatable relative to the housing 4 and/or the indicator device 4d and/or the rotation member 1 for a new selection of a product dose or single dose. Upon resetting, the fourth coupling 4h, 7a becomes uncoupled and the third coupling 2b, 3c becomes coupled, so that the dosing member 3 is non-rotatable relative to the coupling member 2 and the dose display element 10.

As an example, let us assume that after several administrations there are still 76 IU remaining in the product container 14. A maximum of 80 IU can be established with the drive and dosing device. Since the dose limiter is already in contact with the stop at 76 IU, the dosing member 3 is blocked for rotation in the second direction, which would cause an increase of the dose. However, a reduction of the dose is possible by rotating the dosing member 3 in the first direction of rotation.

Upon actuation of the actuation member 7, the dose shown in the indicator device 4d is discharged. Since then the product container 14 has been completely emptied, the drive and dosing device or injection device is discarded in its entirety. Thus it is a one-way, disposable injection device. However, basically speaking, the drive and dosing devices shown herein can also find use in connection with reusable injection devices, in which an emptied product container 14 is exchanged for a new one.

What is claimed is:

1. A drive and dosing device for an injection device for dose selection and administration of a liquid product, where product doses to be administered can be repeatedly selected, the drive and dosing device comprising:
   a housing;
   a dosing member rotatable relative to the housing to select a product dose to be administered;
   an actuation member forming an external surface of the drive and dosing device movable relative to the dosing member for a discharge of the selected product dose;
   a rod-shaped driven member non-rotatable relative to the housing and comprising a distal end for acting on a piston of a product container;
   an abutment of the housing, where the driven member is movable in a discharge direction relative to the abutment during the discharge of the selected product dose;
   at least one spring that acts between the driven member and the abutment, the spring being pretensioned with sufficient energy that it can discharge the maximum dischargeable amount of product from the product container in a plurality of individual discharges;
   a rotation member, wherein rotation of the rotation member relative to the housing causes the at least one spring to move the driven member in the discharge direction to discharge the selected product dose; and
   at least one coupling, wherein during actuation of the actuation member, the at least one coupling releases, thereby allowing the rotation member to rotate relative to the housing, and upon release of the actuation member, the at least one coupling blocks the rotation of the rotation member,
   wherein the at least a spring comprises one compression spring resting against a shoulder of the driven member, and wherein a segment of the driven member extending distal to the shoulder along a lengthwise axis has a length that is greater than the distance between a proximal end of the product container and the piston when the piston is in a position in which the maximum amount of product has been discharged from the product container, or
   wherein the at least one spring comprises a first compression spring and a second compression spring, the first compression spring arranged between the abutment of the housing and an intermediate element movable along the lengthwise axis relative to the housing, and the second compression spring arranged between the intermediate element and the driven member, wherein the intermediate element is spaced from a proximal end of the product container along the lengthwise axis during discharge of the selected product dose, or contacts the proximal end of the product container when a maximum amount of product has been discharged from the product container.

2. The drive and dosing device of claim 1, wherein the compression spring of the at least one spring or the first compression spring of the least one spring does not move in the product container and/or has an outer diameter that exceeds an inner diameter of the product container.

3. The drive and dosing device of claim 1, wherein the shoulder of the driven member joins an inner sleeve of the driven member to an outer sleeve of the driven member, and wherein the one compression spring is disposed in an annular gap formed between the inner sleeve of the driven member and the outer sleeve of the driven member.

4. A drive and dosing device for an injection device for dose selection and administration of a liquid product, where product doses to be administered can be repeatedly selected, the drive and dosing device comprising:
   a housing;
   a dosing member rotatable relative to the housing to select a product dose to be administered;
   an actuation member forming an external surface of the drive and dosing device movable relative to the dosing member for a discharge of the selected product dose;
   a rod-shaped driven member non-rotatable relative to the housing and comprising a distal end for acting on a piston of a product container;
   an abutment of the housing, where the driven member is movable in a discharge direction relative to the abutment during the discharge of the selected product dose;
   at least one spring that acts between the driven member and the abutment, the spring being pretensioned with sufficient energy that it can discharge the maximum dischargeable amount of product from the product container in a plurality of individual discharges;
   a rotation member, wherein rotation of the rotation member relative to the housing causes the at least one spring to move the driven member in the discharge direction to discharge the selected product dose; and
   at least one coupling, wherein during actuation of the actuation member, the at least one coupling releases, thereby allowing the rotation member to rotate relative to the housing, and upon release of the actuation member, the at least one coupling blocks the rotation of the rotation member, and wherein the at least one spring is a torsion spring arranged between the rotation member and the abutment, wherein the torsion spring generates a torque between the rotation member and the abutment.

5. The drive and dosing device of claim 4, wherein the torsion spring is disposed distal to a dose display element and/or a bearing element that is movable along a lengthwise axis relative to the housing, the bearing element being in a threaded engagement with the dose display element.

6. The drive and dosing device of claim 4, wherein the abutment is formed by the housing or an element affixed to the housing and/or the driven member is guided on the housing or the element affixed to the housing.

7. The drive and dosing device of claim 4, further comprising a dose display element comprising a dose scale disposed over a circumference of the dose display element, and an indicator device, wherein the dosing member is rotated relative to the indicator device to select the dose to be administered and slaves the dose display element in rotation such that a value of the dose scale that corresponds to the selected dose can be read from the indicator device.

8. The drive and dosing device of claim 7, wherein the dose display element comprises a stop, which is moved away from a counterstop during a dose increase, and which is moved toward the counterstop during a dose reduction or when the selected product dose is discharged.

9. The drive and dosing device of claim 4, wherein the dosing member is rotationally uncoupled from the at least one spring during dose selection, such that the at least one spring is neither slackened nor tensioned during dose selection.

10. A drive and dosing device for an injection device for dose selection and administration of a liquid product, where product doses to be administered can be repeatedly selected, the drive and dosing device comprising:
    a housing;
    a dosing member rotatable relative to the housing to select a product dose to be administered;
    an actuation member movable relative to the dosing member for a discharge of the selected product dose;
    a driven member non-rotatable relative to the housing and comprising a distal end for acting on a piston of a product container;
    an abutment of the housing, where the driven member is movable in a discharge direction relative to the abutment during the discharge of the selected product dose;
    at least one spring that acts between the driven member and the abutment, the spring at least one being pretensioned with sufficient energy that it can discharge the maximum dischargeable amount of product from the product container in a plurality of individual discharges, wherein the at least one spring comprises a first helical compression spring and a second helical compression spring, the first compression spring arranged between the abutment of the housing and an intermediate element, and the second compression spring arranged between the intermediate element and the driven member, and wherein the intermediate element couples the driven member non-rotatably with the housing;
    a rotation member, wherein rotation of the rotation member relative to the housing causes the at least one spring to move the driven member in the discharge direction to discharge the selected product dose; and
    at least one coupling, wherein during actuation of the actuation member, the at least one coupling releases, thereby allowing the rotation member to rotate relative to the housing, and upon release of the actuation member, the at least one coupling blocks the rotation of the rotation member.

11. The drive and dosing device of claim 10, wherein the actuation member forms an external surface of the drive and dosing device, and wherein the driven member is rod-shaped.

12. The drive and dosing device of claim 10, wherein the intermediate element is engaged with the housing or the abutment of the housing such that the intermediate element is movable along the lengthwise axis relative to the housing and is non-rotatable about the lengthwise axis.

13. The drive and dosing device of claim 10, wherein the intermediate element is engaged with the driven member such that the intermediate element is movable along a lengthwise axis relative to the driven member and is non-rotatable about the lengthwise axis.

14. The drive and dosing device of claim 10, wherein the first compression spring surrounds the driven member and the second compression spring surrounds the driven member.

15. The drive and dosing device of claim 10, wherein the first compression spring surrounds the driven member and the driven member surrounds the second compression spring.

16. The drive and dosing device of claim 15, wherein the driven member is sleeve-shaped, and wherein the intermediate element extends through an elongated slot defined by a wall of the sleeve-shaped driven member, and the intermediate element is moved or is movable in the elongated slot during discharge of the selected product dose.

17. The drive and dosing device of claim 10, wherein the second compression spring is disposed in the housing distal to the first compression spring, where the second compression spring has a smaller outside diameter than the first compression spring.

18. The drive and dosing device of claim 17, wherein at least the second compression spring has a smaller outside diameter than an inner wall of the product container.

* * * * *